United States Patent [19]

Wang et al.

[11] Patent Number: 5,462,545

[45] Date of Patent: Oct. 31, 1995

[54] CATHETER ELECTRODES

[75] Inventors: Paul J. Wang, Chestnut Hill; Peter W. Groeneveld, Cambridge, both of Mass.

[73] Assignee: New England Medical Center Hospitals, Inc., Boston, Mass.

[21] Appl. No.: 189,595

[22] Filed: Jan. 31, 1994

[51] Int. Cl.⁶ .................................................. A61B 17/39
[52] U.S. Cl. ........................... 606/41; 606/48; 128/642; 607/116; 607/122
[58] Field of Search .................................. 606/41, 45–50; 607/100–102, 115, 116, 122, 123; 128/642

[56] References Cited

U.S. PATENT DOCUMENTS

| | | |
|---|---|---|
| 4,532,924 | 8/1985 | Auth et al. ................................. 606/50 |
| 4,660,571 | 4/1987 | Hess et al. . |
| 4,869,248 | 9/1989 | Narula . |
| 4,920,980 | 5/1990 | Jackowski . |
| 4,940,064 | 7/1990 | Desai . |
| 5,016,808 | 5/1991 | Heil, Jr. et al. ........................... 607/122 |
| 5,056,517 | 10/1991 | Fenici . |
| 5,122,136 | 6/1992 | Guglielmi et al. ........................ 606/41 |
| 5,125,928 | 6/1992 | Parins et al. . |
| 5,156,151 | 10/1992 | Imran . |
| 5,239,999 | 8/1993 | Imran ...................................... 128/642 |
| 5,242,441 | 9/1993 | Avitall ....................................... 606/41 |
| 5,327,889 | 7/1994 | Imran ...................................... 128/642 |

OTHER PUBLICATIONS

Kuck et al. "The Split Tip Electrode Catheter . . . " JACC, vol. 21, No. 2, Feb. 2, 1993, p. 1734.

Groeneveld et al., "Panel Electrode 'Pigtail' Catheter using Flexible Electrically Conductive Material: A New Design for Increasing Radiofrequency Ablation Lesion Size?", PACE, vol. 16, Apr. 1993, Part II, NASPE Abstracts, abstract no. 293, p. 923.

Wang et al., "Electrode Panels: A New Design for Radiofrequency Ablation Catheters?", JACC, vol. 21, No. 2, Feb. 2, 1993, p. 265A.

Langberg et al., "Temperature–Guided Radiofrequency Catheter Ablation Using Very Large Distal Electrodes", JACC, vol. 21, No. 2, Feb. 2, 1993, p. 265A.

Kuck et al., "The Split–Tip Electrode Catheter–Improvement in Accessory Pathway Potential Recording", JACC, vol. 21, No. 2, Feb. 2, 1993, p. 173A.

Langberg et al., "Radiofrequency Catheter Ablation: The Effect of Electrode Size on Lesion Volume In Vivo", PACE, vol. 13, Oct. 1990, pp. 1242–1248.

Blouin et al., "The Effect of Electrode Design on the Efficiency of Delivery of Radiofrequency Energy to Cardiac Tissue in Vitro", PACE, vol. 12, Jan. 1989, Part II, pp. 136–143.

*Primary Examiner*—Stephen C. Pellegrino
*Assistant Examiner*—Michael Peffley
*Attorney, Agent, or Firm*—Testa, Hurwitz & Thibeault

[57] ABSTRACT

In one aspect of the invention, an electrode portion of a catheter disposed at a distal portion of the catheter includes two or more electrically conductive panels which: are disposed a substantially fixed radial distance from a directly-underlying axis extending lengthwise through the center of the catheter; are longitudinal strips disposed parallel to the axis, substantially equally around the circumference of the distal portion of the catheter, and substantially isodiametric with the remainder of the catheter; are electrically isolated from each other; are selectively energizable by energy transmitted from a source through the channels to the panels; and can transmit received signals through the channels to means for recording the signals. In another aspect of the invention, a catheter includes an electrically conductive electrode portion which is: disposed at a distal portion of the catheter; energizable; capable of receiving signals; and bent or bendable into a substantially coil configuration.

12 Claims, 6 Drawing Sheets

CATHETER ELECTRODES

FIELD OF THE INVENTION

This invention relates to electrode portions of catheters, and more particularly, to such electrode portions for use in performing medical mapping and/or ablation procedures.

BACKGROUND OF THE INVENTION

An electrode of a catheter can be formed by an electrically conductive material at a distal portion of the catheter. The electrode material typically is stainless steel or platinum, although other electrically conductive materials can be used. In general, the electrode is a band, or series of longitudinally-spaced bands, at the distal portion of the catheter. An electrical wire typically runs through the catheter and is coupled to the electrode to provide electrical energy to the electrode (ablation) and/or to carry recorded signals from the electrode (mapping). Typical electrodes are between about 2.0 and 10.0 mm in length and between about 0.5 to 3.0 mm in diameter.

Medical mapping and ablation procedures can be performed with such catheters by passing the catheter through a body lumen (e.g., a vein, an artery) to a site of interest (e.g., the interior of a heart). Once the catheter is inserted into the body and the electrode is located at the site of interest, electrical energy can be received or emitted by the electrode to map or ablate, respectively. Mapping generally refers to receiving, with the electrode, electrical signals generated by the body (e.g., endocardial signals generated by the heart) and analyzing those signals to determine the source of a medical problem (e.g., an arrhythmia). Once the source and location of the problem has been identified by mapping, tissue at the location is destroyed by ablation to eliminate the problem (e.g., stop the arrhythmia). To ablate tissue, the electrode is placed in contact with the tissue and energized. The energy source can provide a variety of frequencies of energy including radio-frequencies (RF). Energy sources which provide high voltage direct current shock also have been used to energize the electrode. RF energy sources are preferred in some applications because of advantages (e.g., controllability) over DC energy sources.

With RF energy, however, the lesion which can be created is limited to a relatively small size and depth (i.e., volume). To increase the volume and surface area of the lesion, (i) RF energy can be applied multiple times, or for increased periods of time, to the same location, (ii) the output of the source driving the electrode can be increased, or (iii) the length and/or diameter of the electrode can be increased. While each of these three approaches have been attempted, none is entirely ideal. With multiple or extended applications of RF energy, time is lost performing the same operation two or more times or for extended periods of time, and accuracy can suffer because of unintended movement of the electrode between applications. When the output of the source driving the electrode is increased, lesion enlargement occurs but only up to a point because desiccation of tissue causes an abrupt increase in the impedance at the electrode/tissue interface which limits energy transfer to the tissue. Increasing the length and/or diameter of the electrode beyond a certain point (e.g., beyond about 4.0 mm in length and about 2.0 to 3.0 mm in diameter) is not a satisfactory solution because with an increase in surface area of the electrode comes a corresponding decrease in current or power density delivered to the electrode/tissue interface (assuming the output of the source driving the electrode remains substantially constant or limited) and a greater proportion of the electrode not in contact with the location to be ablated.

While standard electrode configurations (e.g., a band, or series of longitudinally-spaced bands, located at a straight, distal portion of the catheter) allow recording along only the longitudinal axis of the straight electrode, they cannot record signals in other dimensions. Thus, in general, electrodes having standard, straight configurations cannot record over large surface areas or volumes of tissue. Similarly, performing ablation with such standard electrodes results in lesions along only the straight longitudinal axis. Lesions having large surface areas or volumes cannot be created because the standard, straight electrodes can neither cover other dimensions nor concentrate energy at the electrode/tissue interface.

SUMMARY OF THE INVENTION

It is an object of the present invention to provide catheter electrodes which can produce lesions having volumes or surface areas greater than that produced by conventional electrodes. It also is an object of this invention to provide catheter electrodes which can record electrical signals more effectively than is possible with standard electrodes. The structure of the disclosed catheter electrodes allows them to outperform electrodes of conventional structure because the current density at the electrode/tissue interface is increased and/or the surface area of the region to be recorded electrically or ablated is increased.

In one aspect, the present invention is directed to an electrode portion of a catheter which is formed of at least two electrically conductive panels which are disposed at a distal portion of the catheter and a substantially fixed radial distance from a directly-underlying axis extending lengthwise through the center of the catheter. Also, the panels are electrically isolated from each other, and each is coupled to a different energy transmitting channel such that the panels are selectively energizable by energy transmitted from a source through the channels to the panels, and they can transmit received signals through the channels to means for recording the signals. In this aspect of the invention, the panels are longitudinal strips disposed parallel to the axis, substantially equally around the circumference of the distal portion of the catheter, and substantially isodiametric with the remainder of the catheter.

The panels not contacting the tissue at all do not need to be energized. In effect, the surface area of the electrode portion can be altered controllably by the selective energization of various combinations of panels. Selective energization of the panels allows the energy to be directed controllably to the location of interest instead of the entire electrode portion. With a conventional electrode, when the entire electrode is energized, ablation or heating of tissue away from the location of interest typically occurs and the current density at the location of interest typically is reduced.

In another aspect, the present invention relates to a catheter having an energizable, electrically conductive electrode portion disposed at a distal portion of the catheter. The electrode portion can receive signals generated by an organ such as the heart, and the distal portion of the catheter can be bent or bendable into a substantially coiled configuration to allow a greater percentage of the electrode portion to be contacted with the tissue of interest such that electrical recordings can be made from a larger surface area and/or a larger area can be ablated.

In still other aspects of the present invention, the paneled or coilable/coiled electrode portion can be used in mapping and/or ablation methods and systems. In addition, the paneled electrode portion can be coilable or coiled as disclosed.

Other objects, aspects, features, and advantages of the invention will become apparent from the following description and from the claims.

DESCRIPTION

Electrode portions of catheters according to the invention typically are used in endocardial mapping and/or ablation procedures and systems to locate and/or eliminate arrhythmias. Ablation can be accomplished by providing radiofrequency (RF) energy to destroy heart tissue causing the arrhythmias. It is possible to use such electrode portions of catheters to perform a variety of other medical mapping and/or ablation procedures besides the treatment of arrhythmias. Also, energy other than RF energy can be used (e.g., electrical, microwave, or laser energy).

Figure 1A:
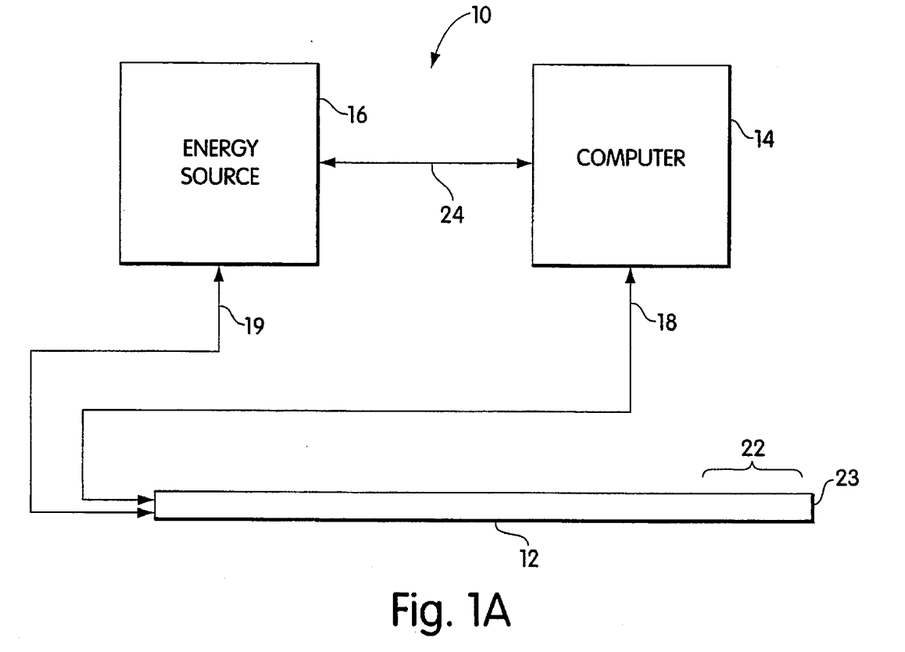
FIGS. 1A and 1B are schematic representations of mapping and/or ablation systems (automated and manual, respectively) in which an electrode portion of a catheter according to the invention can be used.
Figure 1B:
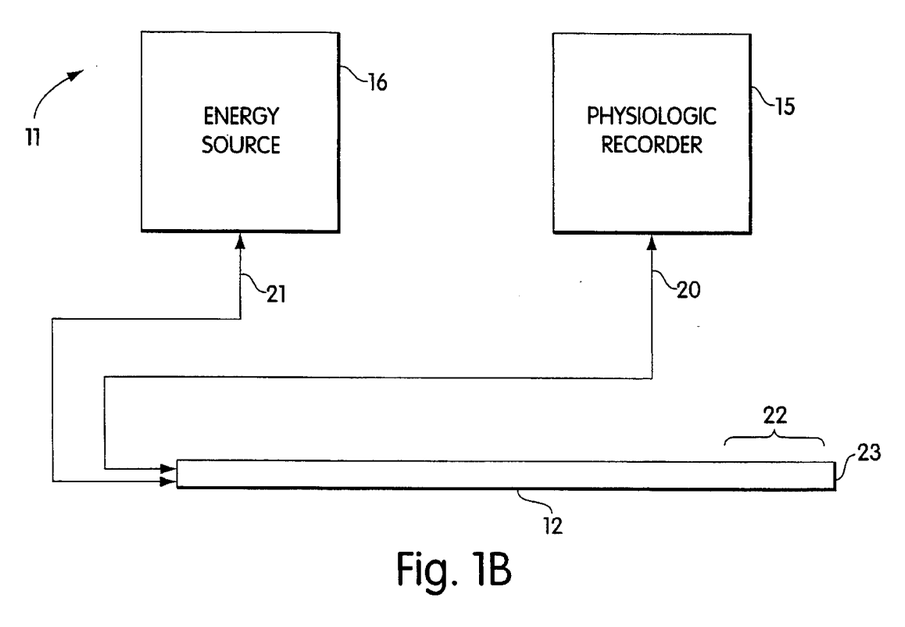

Referring to FIGS. 1A and 1B, an automated mapping and/or ablation system 10 typically includes a catheter 12 coupled to a computer 14 and an energy source 16. Instead of the automated system 10, a manual mapping and/or ablation system 11 can be used. The manual system 11 includes the catheter 12 coupled to the energy source 16 and a physiologic recorder 15. The couplings between the various components are indicated by arrows 18, 19, 20, 21. In both the automated and the manual systems, the catheter 12 typically is a flexible elongated hollow tubular device of a diameter small enough to be passed through blood vessels and into a heart (e.g., between about 0.5 mm to about 3.0 mm in diameter). The catheter 12 can be formed from any flexible material that is inert with respect to the body into which it is inserted. Catheters have been formed from various types of plastics. Disposed at a distal portion 22 of the catheter 12 is one or more electrodes formed of an electrically conductive material which is inert with respect to the body into which it is inserted (e.g., stainless steel or platinum). The electrode(s) can be arranged in a variety of configurations. The term "electrode portion" will be used generally to refer to the electrode(s) regardless of the arrangement thereof. The electrode portion typically ranges in length from about 2.0 mm to about 10.0 mm. The electrode portion can extend all the way to the physical end 23 (i.e., the distal tip) of the catheter 12, or it can terminate before the physical end such that the catheter itself is exposed at the distal tip. Wires, or other energy-transmitting channels or conduits, extend through the catheter to the electrode portion to carry signals to and from the electrode(s) of the electrode portion.

During ablation, the wires carry energy from the source 16 to the electrode portion of the catheter 12. During mapping, the wires carry signals generated by the heart and received by the electrode portion to the computer 14 for recording and/or processing. The computer 14 can record the signals and/or perform mapping functions by analyzing the signals generated by the heart (e.g., with a propagation and delay time procedure) to identify and isolate areas within the heart contributing to an arrhythmia. If the manual system 11 is being employed, the recorded signals are recorder by the physiologic recorder 15 and interpreted by a qualified individual. Regardless of whether the automated or manual system is employed, the goal of recording the signals is to locate the areas of interest. If ablation is required of one or more of the areas of interest, it can be accomplished by placing the electrode portion of the catheter 12 in contact therewith and energizing the electrode(s) of the electrode portion. It also is possible to use one catheter (e.g., the catheter 12) for mapping/recording and then insert a different catheter for ablation purposes. With the automated system 10, the computer 14 generally controls the energy source 16 (as indicated by arrow 24) and most other aspects of the use of the system 10. The computer 14 typically includes a processor, memory, a display, a keyboard and/or mouse, storage device(s), and other components associated with a personal computer or workstation. With the manual system 11, a skilled operator manually controls the system 11. The recorder 15 typically includes display and/or print-out equipment.

In accordance with the invention, the electrode portion disposed at the distal portion 22 of the catheter 12 can be structured as shown in FIGS. 2, 3, and 4. It is important to note that, in general, the drawings are not necessarily to scale and that various components shown in the drawings are not necessarily in proper proportion with respect to each other, emphasis instead being placed upon illustrating the principles of the invention.

Figure 2A:
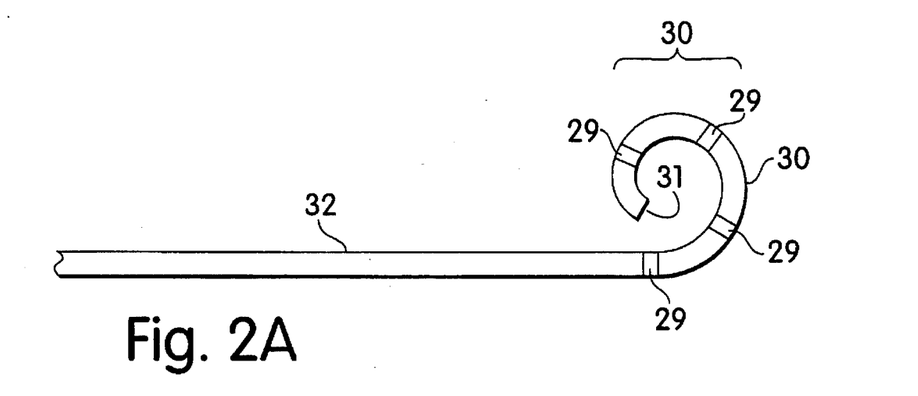
FIGS. 2A–2I are diagrams of embodiments of a coiled or coilable catheter electrode portions according to the invention.
Figure 2B:
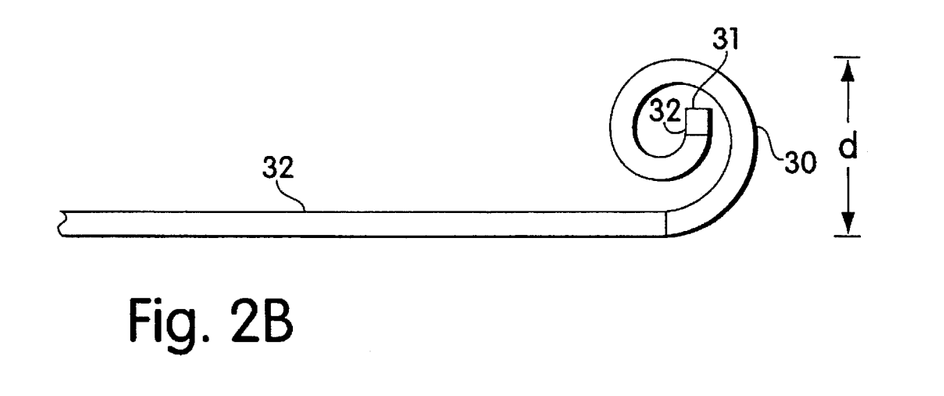
Figure 2C:
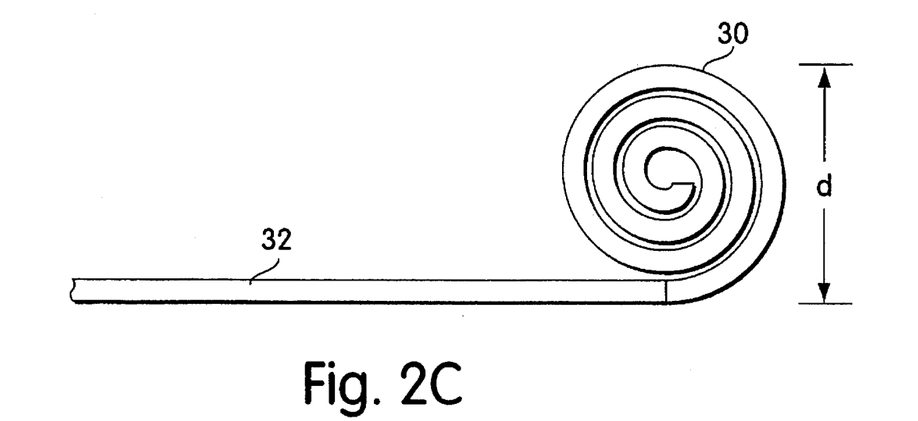

Referring to FIGS. 2A–2E, in some embodiments according to the invention, an electrode portion 30 of a catheter 32 is coiled into a circular (FIG. 2A) or spiral (FIGS. 2B and 2C) configuration. In general, the spiral configuration can have any number of turns. As mentioned previously with reference to FIGS. 1A and 1B, the electrode portion 30 can extend all the way to the physical end 31 (i.e., the distal tip) of the catheter 32 (as shown in FIG. 2A), or it can terminate before the physical end such that the catheter 32 itself is exposed at the distal tip (as shown in FIG. 2B). The electrode portion 30 can be a continuous piece of electrically conductive material (e.g., a band), or it can include any of a variety of other electrode configurations (e.g., a series of bands) including the paneled configuration according to the invention which is described hereinafter with reference to FIG. 3. That is, the numeral 30 identifies the portion of the catheter 32 where the electrode(s) is/are located, but it is not intended to indicate any particular configuration or arrangement of the actual electrode(s). FIG. 2A shows an example of an electrode portion which includes a series of bands, each band indicated by the numeral 29. The actual electrode(s) of the electrode portion 30 can be formed of any electrically conductive material such as a metal, a metal-containing substance, a conductive epoxy, an electrically conductive ink, or combination thereof. In general, the material must be flexible such that it can be coiled, but it must retain its electrical conductivity.

Figure 2D:
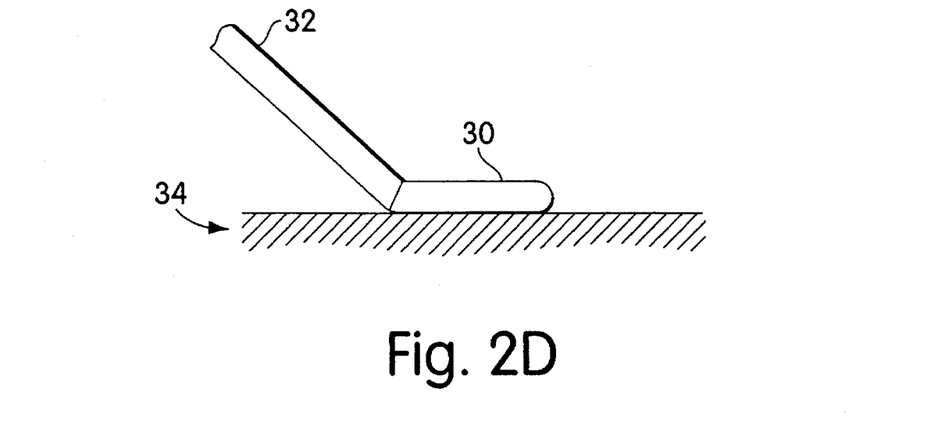
Figure 2E:
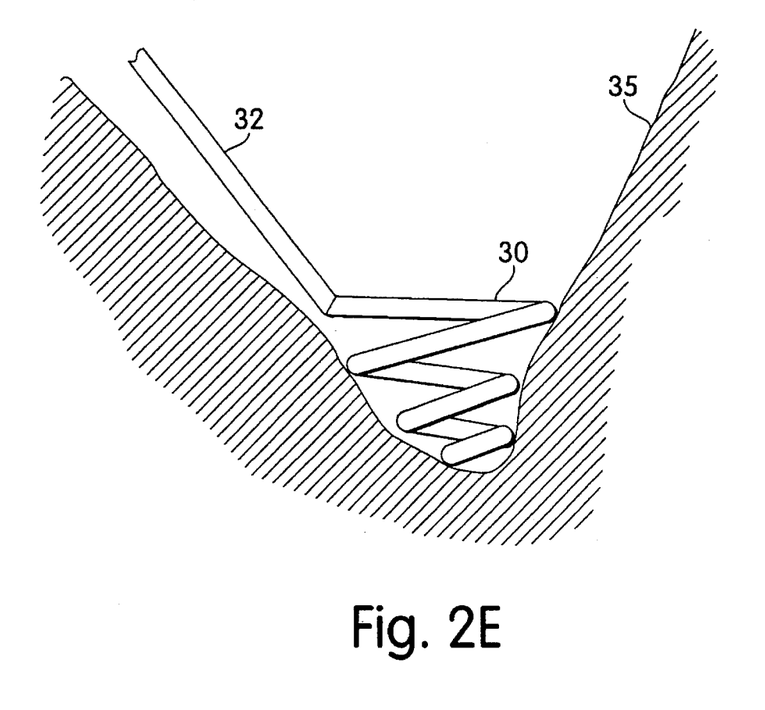

In some embodiments, regardless of whether the electrode portion 30 is coiled into a semi-circular, circular, loosely coupled spiral, tightly coupled spiral, etc. configuration and regardless of whether the electrode portion 30 includes a single band, a series of bands, or any other configuration of electrodes, the coils lie substantially in one plane such that the coiled electrode portion 30 can fully contact tissue 34 to be treated (FIG. 2D). In other embodiments, the coiled electrode portion 30 does not lie in one plane (FIG. 2E) thus allowing it to be contacted with a non-flat tissue surface 35.

The electrode portion 30 of FIGS. 2A–2E can be bent permanently into a desired, predetermined coiled configuration if the diameter (indicated by "d" in FIG. 2B) of that desired coiled configuration is small enough to pass through, for example, veins and blood vessels. If it is desirable not to permanently coil the electrode portion 30, means can be provided which allow an operator to selectively change the shape of the electrode portion 30 from substantially straight to any number of coiled configurations (e.g., slightly bent, partially curled, circular, loosely spiraled, tightly spiraled). Some such means are shown in FIGS. 2F–2I which are cross-sections of distal portions of catheters according to the invention. As mentioned previously with reference to FIGS. 1A, 1B, and 2A–2E, the electrode portion 30 can extend all the way to the physical end (i.e., the distal tip) of the catheter 32 (as shown in FIGS. 2F–2I), or it can terminate before the physical end such that the catheter 32 itself is exposed at the distal tip (as shown in FIG. 2B).

Figure 2F:
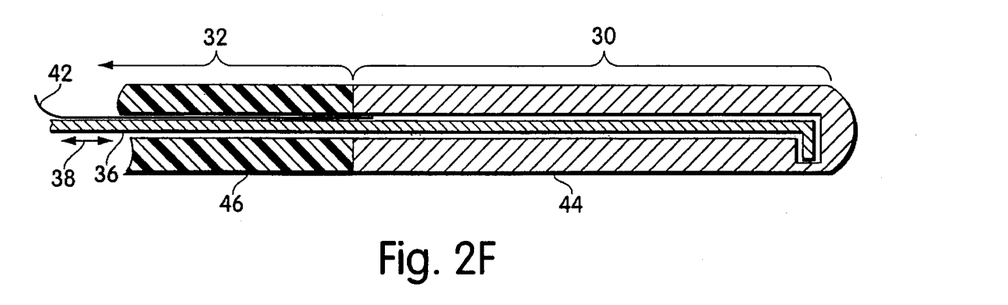
Figure 2G:
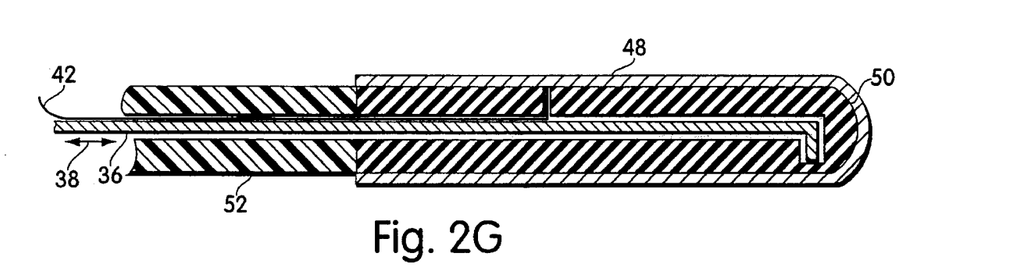
Figure 2H:
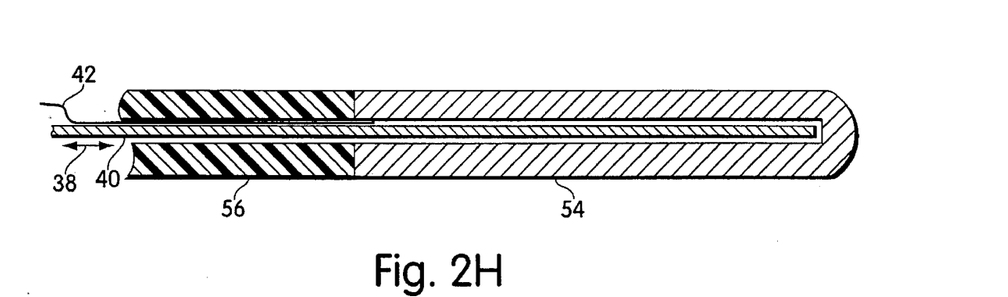
Figure 2I:
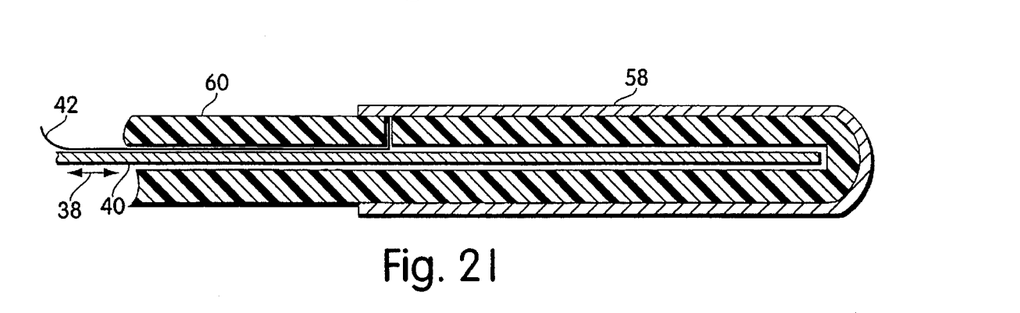

In FIGS. 2F and 2G, the coiling means is a rod 36 extending through the catheter 32 into the electrode portion 30. The rod 36 is locked at the distal end of the electrode such that pushing and/or pulling the rod 36 (as indicated by a double-headed arrow 38) causes the electrode portion 30 to bend into, for example, one of the two coil configurations shown in FIGS. 2A and 2B. In FIGS. 2H and 2I, the coiling means is a core 40 which can be (i) withdrawn from the electrode portion 30 to allow the electrode portion 30 to spring back into a natural, pre-disposed, coiled state (e.g., the coiled state shown in FIG. 2A or 2B) or (ii) inserted into the electrode portion 30 to force the electrode portion 30 out of its natural state into a substantially straight position. With the coiling means of FIGS. 2H and 2I, the electrode portion 30 is formed of materials which have a "memory" such that the electrode portion 30 springs into the desired coiled shape when the core 40 is removed. Such materials are known to those of ordinary skill in the area of medical device design and/or manufacture. It is possible to employ other coiling means besides those shown in FIGS. 2F–2I, the goal being to controllably manipulate the electrode portion into a desired coiled configuration once it reaches the tissue of interest.

While the details of catheter manufacture are known to those of ordinary skill in the area of medical devices, some possible materials are indicated in FIGS. 2F–2I. In FIG. 2F, the electrode portion 30 is an electrically conductive material 44 which can be stretched and bent, and the catheter 32 is flexible plastic 46. In FIG. 2G, the electrode portion 30 is an electrically conductive material 48 formed as a coating or layer over a rubber material 50 where both materials are stretchable and bendable, and the catheter 32 is a flexible plastic 52. In FIG. 2H, the electrode portion 30 is formed of an electrically conductive material 54 which has a "memory" as discussed previously, and the catheter 32 is a flexible plastic 56. In FIG. 2I, the electrode portion 30 is a coating or layer of an electrically conductive material 58 formed over the catheter 32 of flexible plastic 60.

Note that while the electrode portion 30 shown in FIGS. 2F–2I is a single band of electrically conductive material, the electrode portion 30 can include any of a variety of other electrode configurations including, for example, a series of separate electrode bands spaced apart from each other or panels according to the invention (described with reference to FIG. 3).

In FIGS. 2F–2I, signals are carried to and from the electrode portion 30 by one or more wires or other transmitting conduits. Only one wire 42 is shown in each drawing for simplicity. The uncoiled length of the inventive electrode portions of FIG. 2 typically range from about 2.0 mm to about 10.0 mm, although longer or shorter uncoiled lengths can be used depending on the desired diameter ("d" in FIGS. 2B and 2C) of the coil and/or the desired number of turns of the coil. Lengths of up to 30.0 mm or more are possible. The diameter of the inventive electrode portions of FIG. 2 typically range from about 0.5 mm to about 3.0 mm, although smaller or larger diameters can be used depending on the diameter of the lumens through which the electrode portion will be passed.

The disclosed electrode portions (FIG. 2) can be used in the systems of FIGS. 1A and 1B to perform ablation and/or mapping. When used in the system 10 or the system 11, the wire 42 (FIGS. 2F–2I) extends from the source 16 (FIG. 1A or 1B) to the coiled electrode portion 30 to carry the energy output by the source 16 during ablation. Also, the wire 42 typically branches to the computer 14 and carries heart signals from the electrode portion 30 to the computer 14 or recorder 15 during mapping and/or recording. With a coiled or coilable electrode portion according to the invention, more of the surface area of the electrode portion can be placed in contact with the tissue of interest, and thus a greater surface area or volume can be mapped/recorded, or a greater surface area or volume lesion can be created using ablation, than is achievable with a conventional, straight, uncoilable electrode portion of similar length and diameter and driven by a similar power level as the inventive electrode portion.

One specific embodiment according to the invention which was used in an in vitro sheep endocardium model was an electrode having an uncoiled length of 4.0 mm and an uncoiled diameter of about 2.2 mm and formed into a coiled configuration similar to that shown in FIG. 2B. This coiled electrode created an RF lesion having a surface area of $122.0 \pm 11.7$ mm$^2$ and a depth of $4.0 \pm 0.7$ mm (i.e., a volume of $489.0 \pm 110.6$ mm$^3$). The power used for this electrode was $47.3 \pm 1.8$ Watts, which was the highest power below 50 Watts which did not cause an impedance rise. A conventional, straight, uncoilable electrode having a length of 4.0 mm and a diameter of about 2.2 mm also was used to create an RF lesion having a surface area of $47.9 \pm 5.0$ mm$^2$ and a depth of $5.9 \pm 0.7$ mm (i.e., a volume of $283.5 \pm 50.0$ mm$^3$). The power used for this conventional electrode was $43.8 \pm 0.9$ Watts, which was the highest power below 50 Watts which did not cause an impedance rise.

Figure 3A:
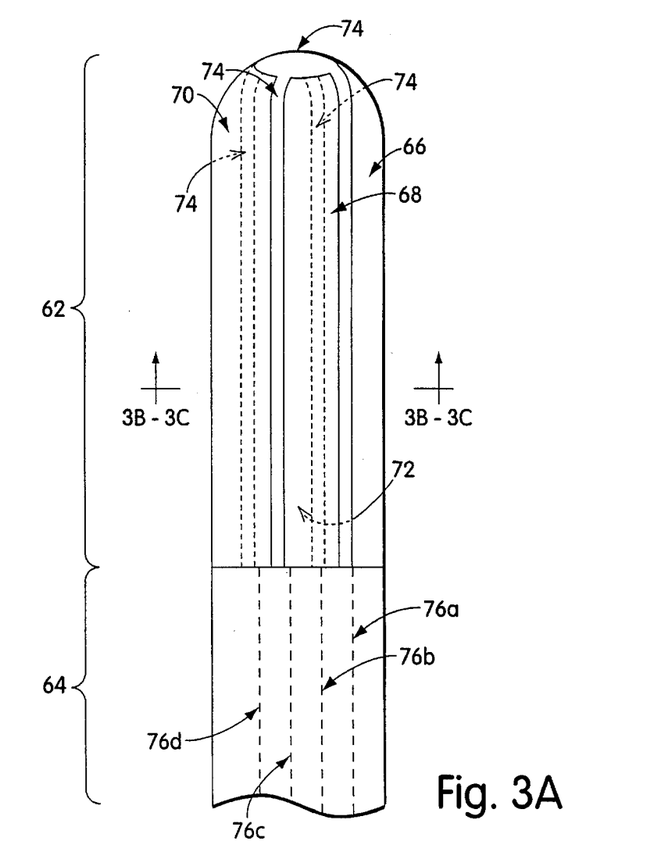
FIGS. 3A–3E are diagrams of embodiments of a paneled catheter electrode portion in accordance with the invention.
Figure 3B:
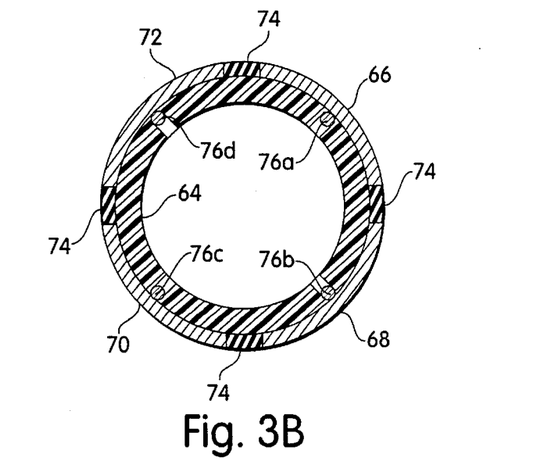
Figure 3C:
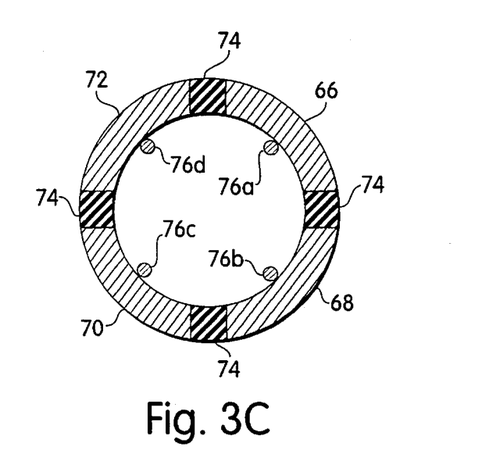

Referring to FIGS. 3A–3C, in some other embodiments according to the invention, an electrode portion 62 of a catheter 64 has four panels 66, 68, 70, and 72 which are longitudinally-disposed electrically-isolated strips. While four panels are shown, it is possible to use as few as two or as many as will physically fit around the circumference of the electrode portion 62 and still be maintained in electrical isolation from each other. The panels can be formed of any of a variety of electrically conductive materials, some of which were mentioned previously. The electrical isolation of panels can be achieved by placing any type of electrically insulating material 74 between the panels. A separate wire (76a, 76b, 76c, and 76d), or other energy-transmitting channel or conduit, extends through the catheter 64 into the electrode portion 62 and connects to each of the panels. The wires allow the panels to be energized individually and in any combination by energy provided by a source (such as the source 16 shown in FIG. 1A which is under the control of the computer 14). The electrode portion 62 can be formed by coating or laying the panels over the catheter (FIG. 3B) or by extending the panels from the catheter 64 (FIG. 3C). (FIGS. 3A and 3B are two possible cross-sectional views of the electrode 62, taken along line 3B–3C in FIG. 3A.) However the electrode portion 62 is formed, the resulting panels are essentially isodiametric with the remainder of the catheter. Also, the resulting panels are fixedly disposed with respect to the catheter; that is, they are disposed a substantially fixed radial distance from a directly-underlying axis (not shown) extending through the center of the catheter 64 all the way to the distal tip of the electrode portion 62. Even if the catheter 64 and/or the electrode portion 62 twists or bends (e.g., as it is coiled and/or as it is pushed through veins to the heart), the panels remain substantially the same fixed radial distance from this directly-underlying imaginary longitudinal axis.

The details of the manufacture of electrodes having the electrically isolated panels according to the invention will be known to those of ordinary skill in the area of medical device design and/or manufacture. Different types of electrically conductive materials can be used successfully for the panels. Various types of electrical insulation can be used to electrically isolate the panels. If a flexible plastic material is used for the body of the catheter (as indicated in FIG. 3B), that material will suffice as an insulator.

The disclosed paneled electrode configurations shown in FIG. 3 can be used in the system 10 of FIG. 1A or the system 11 of FIG. 1B to perform ablation and/or mapping. When used in either system, the wires 76a–76d (FIGS. 3A–3C) extend from the source 16 to one or more of the panels 66, 68, 70, and 72 to carry the energy output by the source 16 during ablation. Also, the wires typically branch to the computer 14 (or the recorder 15) and carry heart signals from one or more of the panels to the computer 14 (or recorder 15) during recording and/or mapping.

With a paneled electrode portion according to the invention, the surface area of the electrode portion can effectively be altered controllably by the selective energization of various combinations of panels. The computer 14 of FIG. 1A can control the source 16 and provide the necessary selectivity by processing signals sensed by each of the panels to determine which panels are contacting tissue and which are not. The computer 14 might do this by exciting each panel and then receiving its response to determine impedance levels at each panel. The computer 14 can control the source 16 such that substantially only the panels contacting the tissue of interest will be energized. Alternatively, an operator can manually determine which panels should be energized and then energize them. Selective energization of the panels allows the energy to be directed controllably to, and generally concentrated at, the location of interest. With a conventional, straight, unpaneled electrode, the entire electrode is energized which typically results in (wasted) ablation or heating of tissue away from the location of interest and also a smaller-than-intended current density delivered to the electrode/tissue interface because of the relatively large percentage of surface area of the conventional electrode which is not in contact with the location of interest. Thus, a paneled electrode portion according to the invention delivers energy more efficiently to the tissue of interest.

One specific embodiment according to the invention which was used in an in vitro sheep endocardium model was a three-panel electrode having a length of 5.0 mm and a diameter of about 2.2 mm. The panels were strips similar to those shown in FIG. 3A. This three-panel electrode was applied for thirty seconds to create an RF lesion having a length of $7.1\pm0.7$ mm, a width of $3.8\pm0.6$ mm, and a depth of $2.5\pm0.5$ mm (i.e., a volume of $54.3\pm15.1$ mm$^3$). The power used for this three-panel electrode was $7.9\pm1.5$ Watts, which was the highest power which did not cause an impedance rise. A similar electrode also was used. This second electrode was a 10.0 mm long three-panel electrode according to the invention having a diameter of about 2.2 mm. This second three-panel electrode was applied for thirty seconds to create an RF lesion having a length of $10.8\pm0.8$ mm, a width of $3.6\pm0.4$ mm, and a depth of $2.1\pm0.8$ mm (i.e., a volume of $70.2\pm27.0$ mm$^3$). The power used for this three-panel electrode was $14.1\pm3.2$ Watts, which was the highest power which did not cause an impedance rise.

Figure 3D:
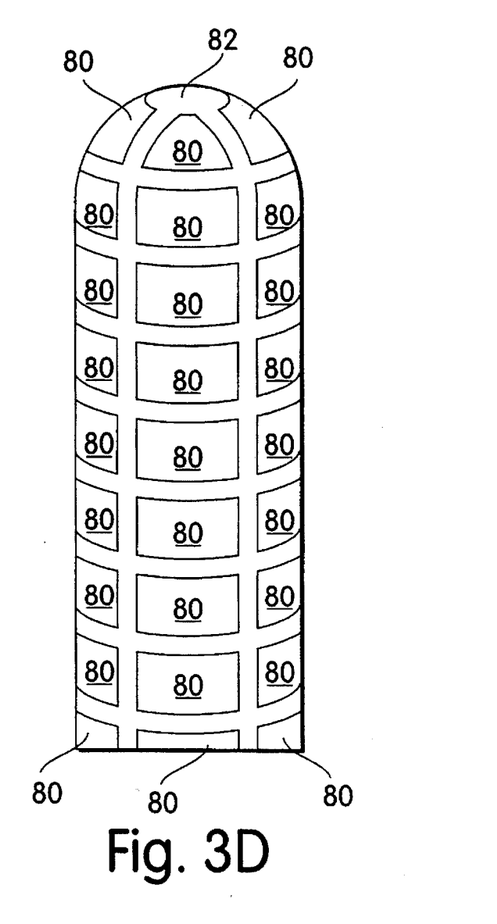
Figure 3E:
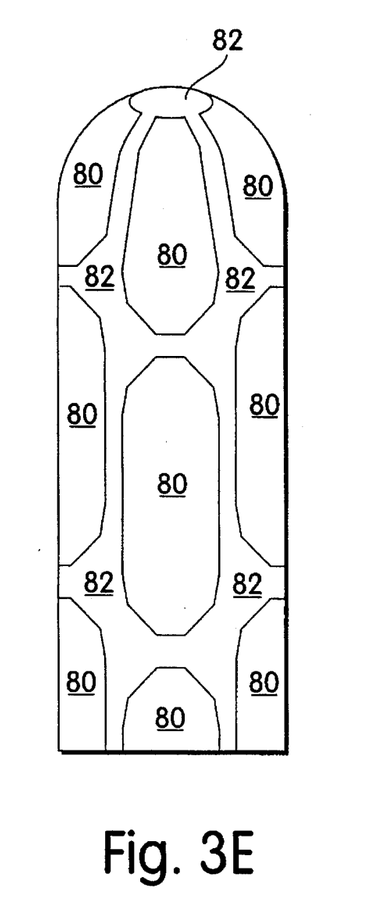

The panels on paneled catheter electrodes in accordance with the invention can be varied in number, shape, and arrangement. While the panels shown in FIG. 3A are longitudinally-arranged strips, a variety of other configurations are possible. It is possible to employ any shape and arrangement of panels which results in a paneled electrode portion of a catheter which has a controllably alterable active surface area (by selectively energizing various combinations of panels) such that energy can be directed controllably to, and generally concentrated at, a particular location of interest. Note that the more the number of panels, the more the number of wires extending through the catheter to each of the panels to carry signals to and from each of the panels. Referring to FIGS. 3D and 3E, two additional panel arrangements are shown where the electrically conductive panels are identified by the numeral 80 and the electrically insulating material is identified by the numeral 82. Note that to be most effective, a configuration should not include panels which extend continuously around the catheter such that energization of one or more of those panels results in energy being delivered to a portion of the panel(s) not substantially in contact with the electrode/tissue interface of interest.

Other embodiments of catheter electrode portions according to the invention include paneled electrode portions (FIG. 3) which are coiled or coilable (FIG. 2). Various coiling means can be employed, as described previously, if the paneled electrode portion is not bent permanently into a predetermined coiled configuration. A catheter having a coiled or coilable paneled electrode portion can be used as described previously with respect to FIG. 2, but in this case, an even larger lesion volume may be created because the advantages of the paneling and the coiling generally combine to enhance the results beyond those achievable with paneling or coiling alone.

Other modifications and implementations will occur to those skilled in the art without departing from the spirit and the scope of the invention as claimed. Accordingly, the invention is to be defined not by the preceding illustrative description but instead by the following claims.

What is claimed is:

1. A catheter electrode, comprising:
   at least three electrically conductive panels which are:
   disposed at a distal portion of a catheter and in a substantially coil configuration; disposed a substantially fixed radial distance from a directly-underlying axis extending lengthwise through the center of the catheter;
   disposed substantially equally around the circumference of the distal portion of the catheter, and substantially isodiametric with the reminder of the catheter;
   electrically isolated from each other; and
   each coupled to a first end of a different energy transmitting channel which has a second end couplable to an energy source and a recorder such that the panels; are selectively energizable individually and in any combination by energy transmitted from the source through the channels to the panels, and can transmit received signals through the channels to the recorder.

2. The catheter electrode of claim 1 wherein the panels comprise longitudinal strips disposed along the length of the axis and substantially equally around the circumference of the distal portion of the catheter.

3. A method for increasing lesion size, comprising:
(A) providing an electrode comprising at least three electrically conductive panels which are:
  disposed at a distal portion of a catheter and in a substantially coil configuration;
  disposed a substantially fixed radial distance from a directly-underlying axis extending lengthwise through the center of the catheter;
  disposed substantially equally around the circumference of the distal portion of the catheter, and substantially isodiametric with the remainder of the catheter;
  electrically isolated from each other; and
  each coupled to a first end of a different energy transmitting channel which has a second end couplable to an energy source and a recorder such that the panels: are selectively energizable individually and in any combination by energy transmitted from the source through the channels to the panels, and can transmit received signals through the channels to the recorder;
(B) placing one or more of the panels in contact with tissue to be ablated; and
(C) selectively energizing the panels substantially contacting the tissue to create a lesion in the tissue.

4. The method of claim 3 further comprising bending the electrode into a substantially coil configuration such that a larger area of tissue can be contacted by the one or more panels.

5. The method of claim 3 further comprising receiving, with one or more of the panels, signals generated by an organ; and analyzing the received signals to determine the tissue to be ablated.

6. The method of claim 3 wherein the panels comprise longitudinal strips disposed along the length of the axis and substantially equally around the circumference of the distal portion of the catheter.

7. A catheter electrode, comprising:
at least three electrically conductive panels which are:
  disposed at a distal portion of a catheter;
  bendable into a substantially coil configuration;
  disposed a substantially fixed radial distance from a directly-underlying axis extending lengthwise through the center of the catheter;
  disposed substantially equally around the circumference of the distal portion of the catheter, and substantially isodiametric with the remainder of the catheter;
  electrically isolated from each other; and
  each coupled to a first end of a different energy transmitting channel which has a second end couplable to an energy source and a recorder such that the panels: are selectively energizable individually and in any combination by energy transmitted from the source through the channels to the panels, and can transmit received signals through the channels to the recorder.

8. The catheter electrode of claim 7 wherein the catheter further comprises means for bending the panels and the distal portion into the substantially coil configuration.

9. The catheter electrode of claim 7 wherein the panels comprise longitudinal strips disposed along the length of the axis and substantially equally around the circumference of the distal portion of the catheter.

10. A method for creating lesions, comprising:
(A) providing an electrode comprising at least three electrically conductive panels which are:
  disposed at a distal portion of a catheter;
  disposed a substantially fixed radial distance from a directly-underlying axis extending lengthwise through the center of the catheter;
  disposed substantially equally around the circumference of the distal portion of the catheter, and substantially isodiametric with the remainder of the catheter;
  electrically isolated from each other; and
  each coupled to a first end of a different energy transmitting channel which has a second end couplable to an energy source and a recorder such that the panels: are selectively energizable individually and in any combination by energy transmitted from the source through the channels to the panels, and can transmit received signals through the channels to the recorder;
(B) bending the panels at the distal portion of the catheter into a substantially coil configuration;
(C) placing one or more of the panels in contact with tissue to be ablated; and
(D) selectively energizing the panels substantially contacting the tissue to create a lesion in the tissue.

11. The method of claim 10 further comprising:
receiving, with one or more of the panels, signals generated by an organ; and
analyzing the received signals to determine the tissue to be ablated.

12. The method of claim 10 wherein the panels comprise longitudinal strips disposed along the length of the axis and substantially equally around the circumference of the distal portion of the catheter.

* * * * *